United States Patent [19]

Nishi et al.

[11] Patent Number: 5,541,198
[45] Date of Patent: Jul. 30, 1996

[54] CARBOSTYRIL DERIVATIVES

[75] Inventors: Takao Nishi; Tetsuyuki Uno; Yoshio Shu; Katsumi Tamura; Minoru Okada, all of Tokushima, Japan

[73] Assignee: Otsuka Pharmaceutical Co., Ltd., Tokyo, Japan

[21] Appl. No.: 367,196

[22] PCT Filed: May 11, 1994

[86] PCT No.: PCT/JP94/00760

§ 371 Date: Jan. 18, 1995

§ 102(e) Date: Jan. 18, 1995

[87] PCT Pub. No.: WO94/26732

PCT Pub. Date: Nov. 24, 1994

[30] Foreign Application Priority Data

May 19, 1993 [JP] Japan ..................... 5-116764

[51] Int. Cl.[6] ..................... A61K 31/47; C07D 401/12
[52] U.S. Cl. ..................... 514/312; 546/157; 546/158
[58] Field of Search ..................... 546/157, 158; 514/312

[56] References Cited

U.S. PATENT DOCUMENTS 5,008,274 4/1991 Nishi et al. ..................... 514/312

FOREIGN PATENT DOCUMENTS 57-159778 10/1982 Japan.

OTHER PUBLICATIONS

"3,4–Dihydroquinolin–2(1H)–one as Combined Inhibitors of Thromboxane $A_2$ Synthase and cAMP Phosphodiesterase[1]", G. Martinez et al., J. Med. Chem, 35:4(620–628) 1992.

"A Platelet–Dependent Serum Factor That Stimulates the Proliferation of Arterial Smooth Muscle Cells In Vitro", R. Ross et al, Proc. Nat. Acad. Sci USA, 71:4(1207–1210) 1974.

"The Pathogenesis of Atherosclerosis—An Update", R. Ross, The New England Journal of Medicine, 314:8(488–500) 1986.

*Primary Examiner*—C. Warren Ivy
*Assistant Examiner*—Evelyn Huang
*Attorney, Agent, or Firm*—Finnegan, Henderson, Farabow, Garrett & Dunner

[57] ABSTRACT

Carbostyril derivatives useful for inhibiting the adhesion of platelets represented by general formula

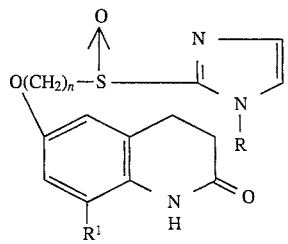

[wherein, $R^1$ is a hydrogen atom, a fluorine atom or a methyl group; R is a group of the formula

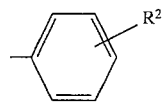

($R^2$ is a methyl group, a trifluoromethyl group or a nitro group), or a group of the formula

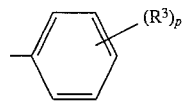

($R^3$ is a fluorine atom and p is an integer of 2 or 3); and n is an integer of 2 or 3], or salts thereof.

Said carbostyril derivatives or salts are useful as an agent for inhibiting the adhesion of platelets.

13 Claims, No Drawings

CARBOSTYRIL DERIVATIVES

This application is the National phase of PCT/JP94/00760 filed on May 11, 1994.

INDUSTRIAL FIELD OF UTILIZATION

The present invention relates to novel carbostyril derivatives.

DISCLOSURE OF THE INVENTION

The carbostyril derivatives of the present invention are represented by the following general formula (1):

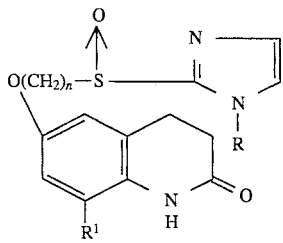

[wherein, $R^1$ is a hydrogen atom, a fluorine atom or a methyl group; R is a group of the formula

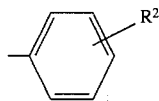

($R^2$ is a methyl group, a trifluoromethyl group or a nitro group), or a group of the formula

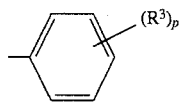

($R^3$ is a fluorine atom and p is an integer of 2 or 3); and n is an integer of 2 or 3].

The carbostyril derivatives of the present invention have a strong activity for inhibiting the adhesion of platelets and show low adverse effects to the cardiovascular system, etc., and are useful agent for treatment and prevention of arteriosclerotic diseases and thrombotic diseases.

PRIOR ART

Japanese Patent Application Kokai (Laid-Open) No. 45220/1988 (corresponding to EP-A-0240015 and U.S. Pat. No. 5,008,274) discloses the carbostyril compounds represented by the following general formula:

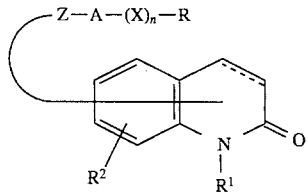

(wherein, R is an unsaturated heterocyclic residual group having 1 to 4 hetero atoms selected from the group consisting of a nitrogen atom, an oxygen atom and a sulfur atom; said unsaturated heterocyclic residual group may have, on the heterocyclic residual ring, 1 to 3 substituents selected from the group consisting of an oxo group; a thio group; a phenyl group; a phenyl group which may have, on the phenyl ring, 1 to 3 substituents selected from the group consisting of a lower alkyl group, a halo-lower alkyl group, a halogen atom, a hydroxyl group, an amino group, a lower alkylamino group, a carboxyl group and a lower alkoxy group; a cycloalkyl group; a phenylthio group; a lower alkyl group; a lower alkyl group having 1 to 2 substituents selected from the group consisting of an amino group, a lower alkylamino group and a carboxyl group; an amino group; a hydroxyl group; a cyano group; a carboxyl group; a lower alkoxycarbonyl group; a phenyl-lower alkyl group which may have hydroxyl groups as the substituents on the phenyl ring; a phenylsulfonyl group which may have lower alkyl groups as the substituents on the phenyl ring; a lower alkoxy-substituted phenyl-lower alkyl group; a lower alkylthio group; a lower alkenyl group; a lower alkoxy group and a pyridyl group;

$R^1$ is a hydrogen atom, a lower alkyl group or a phenyl-lower alkyl group;

$R^2$ is a hydrogen atom, a halogen atom, a lower alkylsulfonyloxy group, a lower alkoxy group or a hydroxyl group;

Z is an oxygen atom, a sulfur atom, a group of the formula

a group of the formula

a group of the formula

(wherein $R^3$ is a hydrogen atom or a lower alkyl group) or a group of the formula —NH—;

A is a lower alkylene group;

X is an oxygen atom, a sulfur atom, a group of the formula —SO— or a group of the formula —$SO_2$—;

n is an integer of 0 or 1; and the carbon-carbon bond between 3- and 4-positions in the carbostyril skeleton is a single or double bond).

Since said carbostyril derivatives and salt thereof possess activities for inhibition of thrombotic adhesion, they can be used not only for the treatment and prevention of arteriosclerosis, ischemic heart disease, chronic arterial obstruction, and acute or chronic nephritis, but also in the treatment of artificial dialysis and implantation of artificial organs, etc.

Some of the carbostyril derivatives of the present invention represented by the above general formula (1) are similar, in chemical structure, to the above-mentioned carbostyril compounds disclosed in prior art literatures, but none of the present carbostyril derivatives is disclosed therein. Further, as shown in the pharmacological test results given later, the present carbostyril derivatives have a very strong activity for inhibiting the adhesion of platelets, even when compared with the prior art compounds having chemical structures most similar to those of the present carbostyril derivatives.

DETAILED DESCRIPTION OF THE INVENTION

Ateriosclerosis is an arterial lesion associated with the hypertrophy, sclerosis and regression of arterial wall, is often complicated by thrombosis, and allows the tissues of various organs (e.g., brain, heart and peripheral blood vessels) to have ischemic diseases. As well known, platelets are deeply connected with the onset and progress of arteriosclerosis (cf., Russell Ross et al., Proc. Natl. Acad. Sci. USA, Vol. 71, p. 1207, 1974; and Russell Ross et al., New Engl. J. Med. Vol. 314, p. 488, 1986). That is, in the first stage of arteriosclerosis onset, endothelial cells of artery are peeled by disturbance factors such as hypertension, hyperlipidemia, smoking, hormones, bacteria, serotonin, thromboxane $A_2$ and the like; and platelets adhere onto the injured arterial walls. This adhesion of platelets is an initial reaction in the formation of thrombus. The adhered platelets cause agglutination with other platelets via fibrinogen and, from the granules in the agglutinated platelets, there are released, outside the cells, physiologically active substances such as thromoxane $A_2$, serotonin, ADP (adenosine diphosphate), PDGF (platelet-derived growth factor) and the like. The released thromboxane $A_2$, serotonin and ADP injure the tunica intima of artery and the PDGF gives rise to (1) the migration of smooth muscle cells of arterial tunica media into arterial tunica intima and (2) the proliferation of smooth muscle cells, which invites the hypertrophy of arterial tunica intima and promotes arteriosclerosis. Hence, substances having an activity for inhibiting the adhesion of platelets can inhibit the hypertrophy of arterial tunica intima or the agglunitization of platelets and thereby can be effectively used for the treatment and prevention of ischemic diseases such as arteriosclerosis and thrombosis.

A number of antiplatelets drugs have been developed as a remedy for ischemic diseases. They are for the inhibition of agglutination of platelets and inhibit the formation of thrombus in blood stream, but do not inhibit the hypertrophy of arterial tunica intima. The carbostyril derivatives of the present invention inhibit both the formation of thrombus and the hypertrophy of arterial tunica intima and thereby maintains normal blood stream. In clinical applications, the present carbostyril derivatives can be effectively used for the treatment and prevention of cerebral diseases such as cerebral infarction, transient cerebral ischemic attack, cerebral arteriosclerosis and the like; heart diseases such as myocardial infarction, cardiac angina and the like; peripheral circulatory diseases such as chronic arteriosclerosis, Bueger's disease and the like; renal diseases such as glomerulonephritis, renal hypertension and the like; and so forth. The present carbostyril derivatives can also be used for blood circulatory reconstruction operations such as artificial blood vessel transplantation and the like; prevention of restenosis in percutaneous blood circulation reconstructive operations such as PTA (percutaneous transluminal angioplasty), PTCA (percutaneous transluminal coronary angioplasty), PTCR (percutaneous transluminal coronary recanalization) and the like; improvements in blood circulation in artificial dialysis, embedding of artificial organ, intermittent claudication, collagen disease, diabetes mellitus, occupational health hazard due to local vibration, etc.; and improvements in neurotic symptoms and syndromes.

The present compounds represented by general formula (1) include:

① compounds of general formula (1) wherein $R^1$ is a hydrogen atom and R is a group of the formula

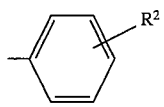

($R^2$ is the same as defined above),

② compounds of general formula (1) wherein $R^1$ is a hydrogen atom and R is a group of the formula

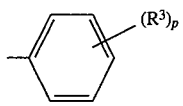

($R^3$ and p are the same as defined above),

③ compounds of general formula (1) wherein $R^1$ is a fluorine atom and R is a group of the formula

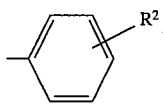

($R^2$ is the same as defined above),

④ compounds of general formula (1) wherein $R^1$ is a fluorine atom and R is a group of the formula

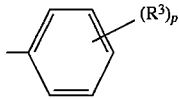

($R^3$ and p are the same as defined above),

⑤ compounds of general formula (1) wherein $R^1$ is a methyl group and R is a group of the formula

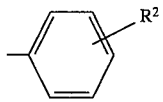

($R^2$ is the same as defined above), and

⑥ compounds of general formula (1) wherein $R^1$ is a methyl group and R is a group of the formula

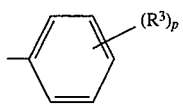

($R^3$ and p are the same as defined above).

In the above compounds, $R^1$ is particularly preferably a hydrogen atom; the group of the formula

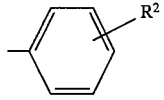

is particularly preferably 2-methylphenyl, 2-nitrophenyl or 2-trifluoromethylphenyl; the group of the formula

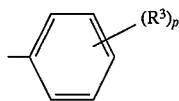

is particularly preferably 2,3,4-trifluorophenyl, 2,4,6-trifluorophenyl, 2,4,5-trifluorophenyl or 2,4-difluorophenyl; and n is particularly preferably 3.

The present carbostyril derivatives include racemic compounds, S—(+) compounds and R—(−) compounds. Among of them, S—(+) compounds are particularly preferable.

The carbostyril derivatives of general formula (1) according to the present invention can be produced by various processes. Examples of the processes include those represented by the following reaction formulas.

Reaction formula-1

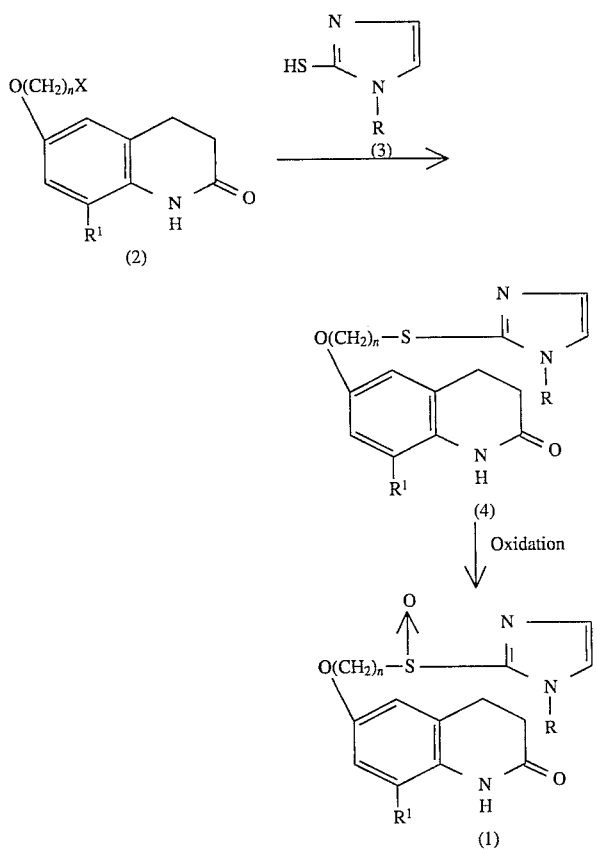

(wherein, R, R¹ and n are the same as defined above; and X is a halogen atom, a lower alkanesulfonyloxy group, an arylsulfonyloxy group or an aralkylsulfonyloxy group).

Specific examples of the lower alkanesulfonyloxy group represented by X are methanesulfonyloxy, ethanesulfonyloxy, propanesulfonyloxy, isopropanesulfonyloxy, butanesulfonyloxy, tert-butanesulfonyloxy, pentanesulfonyloxy and hexanesulfonyloxy groups. Specific examples of the arylsulfonyloxy group are phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy and α-naphthylsulfonyloxy groups. Specific examples of the aralkylsulfonyloxy group are benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy and α-naphthylmethylsulfonyloxy groups. Specific examples of the halogen atom are fluorine, chlorine, bromine and iodine atoms.

The reaction of the compound of general formula (2) with the compound of general formula (3) can be conducted in an appropriate solvent or in the absence of any solvent, in the presence of a basic compound. The basic compound can be selected widely from known basic compounds and includes inorganic bases such as sodium hydroxide, potassium hydroxide, sodium carbonate, potassium carbonate, sodium hydrogencarbonate, potassium hydrogencarbonate, silver carbonate and the like; alkali metals such as sodium, potassium and the like; alcholates such as sodium methylate, sodium ethylate, potassium t-butoxide and the like; and organic bases such as triethylamine, pyridine, N,N-dimethylamine, N-methylmorpholine, 4-dimethylaminopyridine, 1,5-diazabicyclo[4,3,0]nonene-5 (DBN), 1,8-diazabcyclo[5,4,0]undecene-7 (DBU), 1,4-diazabicyclo[2,2,2 octane (DABCO) and the like. As to the solvent, any one of inert solvents which does not give adverse effect to the reaction can be used and includes, for example, alcohols such as methanol, ethanol, propanol, isopropanol, butanol, ethylene glycol and the like; ethers such as dimethyl ether, tetrahydrofuran, dioxane, monoglyme, diglyme and the like; ketones such as acetone, methyl ethyl ketone and the like; aromatic hydrocarbons such as benzene, toluene, xylene and the like; esters such as methyl acetate, ethyl acetate and the like; and aprotic polar solvents such as N,N-dimethylformamide (DMF), dimethyl sulfoxide (DMSO), hexamethylphosphoric triamide (HMPA) and the like. The reaction may be conducted in the presence of a metal iodide such as sodium iodide, potassium iodide or the like. The proportions of the compound (2) and the compound (3) used in the above reaction have no particular restriction and can be appropriately selected from a wide range thus, desirably, the latter compound is used in an amount of generally about 1–5 moles, preferably about 1–3 moles per mole of the former compound. The reaction temperature may not particularly restricted, and is generally about room temperature to 200° C., preferably about 50°–150° C. The reaction is completed generally in about 5 minutes to 30 hours.

The oxidation of the compound (4) is conducted in the presence of an oxidizing agent, in an appropriate solvent. The oxidizing agent can be any known oxidizing agent capable of oxidizing a sulfide group into a sulfoxide group, and includes, for example, peracids such as performic acid, peracetic acid, trifluoroperacetic acid, perbenzoic acid, m-chloroperbenzoic acid, o-carbonylperbenzoic acid and the like; hydrogen peroxide; combinations of (1) an alkylhydroperoxide such as tert-butyl hydroperoxide, cumene hydroperoxide or the like and (2) a titanium tetraalkoxide such as titanium tetraisopropoxide or the like; bichromic acid; bichromic acid salts such as sodium bichromate, potassium bichromate and the like; permanganic acid; and permanganic acid salts such as sodium permanganate, potassium permanganate and the like. The solvent includes water; organic acids such as formic acid, acetic acid, trifluoroacetic acid and the like; alcohols such as methanol, ethanol and the like; halogenated hydrocarbons such as chloroform, dichloroethane, dichloromethane and the like; and mixtures thereof. The reaction proceeds favorably generally at −20° C. to 40° C., preferably at about −20° C. to room temperature and is complete generally in about 0.5–70 hours. The desirable amount of the oxidizing agent used is generally at least 1 mole, preferably about 1–1.5 moles per mole of the compound (4). The amount is preferably about 1–5 moles per mole of the compound (4) when the oxidizing agent used is a combination of an alkyl hydroperoxide and a titanium tetraalkoxide.

In the above reaction, by adding, to the reaction system, an agent for asymmetric induction such as optically active dialkyl tartrates [e.g., D—(−) diethyl tartrate or L—(+) diethyl tartrate] or naphthols (e.g., binaphthol), there can be obtained an optically active compound (1) at a high yield and at a high purity. The optically active compound (1) is subjected to several times of recrystallization by an ordinary method, whereby it can be made into a compound (1) of higher purity. The amount of the agent for asymmetric induction used is desirably about 1–5 moles per mole of the compound (4). The oxidizing agent used when an optically active compound (1) is obtained, is particularly preferably a combination of an alkyl hydroperoxide and a titanium tetraalkoxide. When this oxidizing agent is used, the reaction proceeds favorably by the addition of a molecular sieve or water in an amount of 0.1–1 equivalent relative to the compound (4).

of ordinary use, such as platinum oxide, platinum, platinum black, palladium, palladium black, palladium-carbon, Raney nickel and the like. The desirable amount of the catalyst used is generally about 0.02–1 time the weight of the compound (7) used. The catalytic reduction is conducted in a solvent such as water, lower alcohol (e.g., methanol, ethanol or isopropanol), ether (e.g., tetrahydrofuran or diethyl ether) or the like in a hydrogen atmosphere of generally 1–20 atm., preferably 1–10 atom. with sufficient shaking. The reduction is conducted generally at −30° C. to the boiling point of the solvent used, preferably at about 0°–100° C. and is complete generally in about 0.5–20 hours. The reaction proceeds

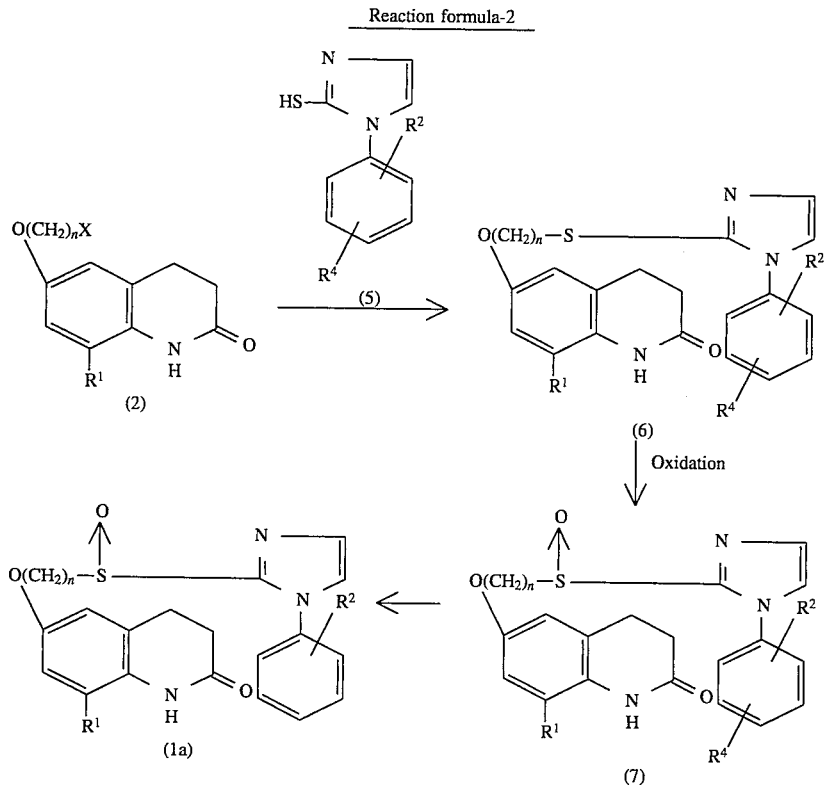

Reaction formula-2

(wherein, $R^1$, $R^2$, n and X are the same as defined above; and $R^4$ is a chlorine atom, a bromine atom or an iodine atom).

The reaction of the compound (2) with the compound (5) and the oxidation of the compound (6) can be conducted under the same conditions as in the reaction of the compound (2) with the compound (3) and the oxidation of the compound (4) in the Reaction formula-1, respectively.

The reaction for converting the compound (7) into a compound (1a) can be conducted by catalytic reduction. As to the catalyst for catalytic reduction, there can be used those favorably by the addition of a basic compound (e.g., triethylamine) to the reaction system.

The compound (7) is useful as an intermediate for synthesis of compound (1). When there is used, for example, an optically active compound (7) as said intermediate, an optically active compound (1) can be obtained at a high yield at a high purity.

Reaction formula-3

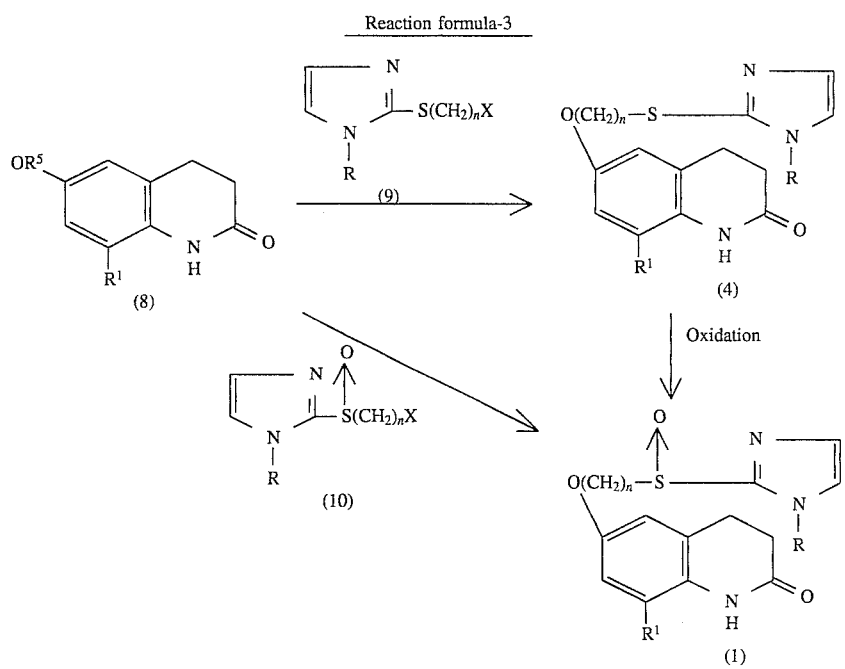

(wherein, R, $R^1$, n and X are the same as defined above; and $R^5$ is a hydrogen atom or an alkali metal such as sodium, potassium or the like).

The reaction of the compound (8) with the compound (9) and the reaction of the compound (8) with the compound (10) are conducted under the same conditions as employed in the reaction of the compound (2) with the compound (3) in the Reaction formula-1, except that the compound (8) is used in an amount of generally about 1–5 moles, preferably about 1–2 moles per mole of the compound (9) or the compound (10). The oxidation of the compound (4) was described in the Reaction formula-1.

Reaction formula-4

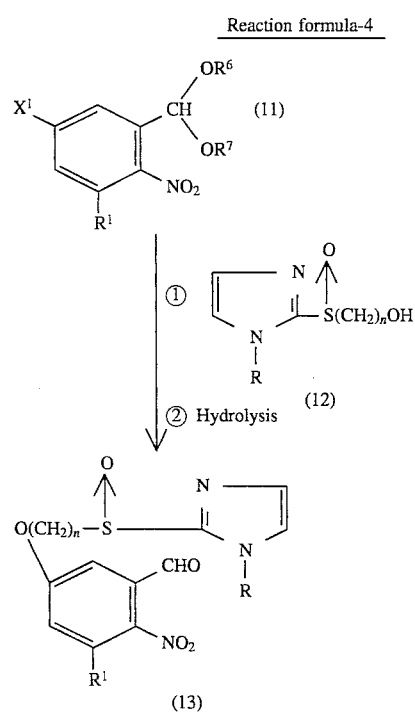

-continued
Reaction formula-4

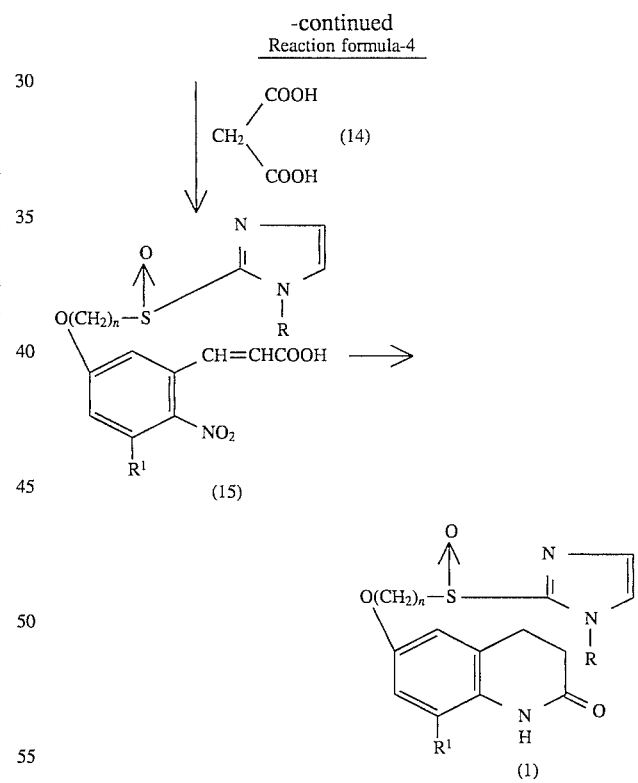

(wherein, $R^1$ and n are the same as defined above; $X^1$ is a halogen atom or an arylsulfonyloxy group; and $R^6$ and $R^7$ independently represent a lower alkyl group).

The reaction of the compound (11) with the compound (12) can be conducted in the presence of a solvent. The solvent includes, for example, aromatic hydrocarbons such as benzene, toluene, xylene and the like; lower alcohols such as methanol, ethanol, isopropanol and the like; ethers such as dioxane, tetrahydrofuran, ethylene glycol dimethyl ether, diethyl ether and the like; and polar solvents such as N-methylpyrrolidone, dimethylformamide, dimethyl sulfoxide, hexamethylphosphoric triamide and the like. The reaction may use a basic compound as an acid remover to allow the reaction to proceed more favorably. The basic compound can be exemplified by potassium carbonate, sodium carbonate, sodium hydroxide, sodium hydrogen carbonate, sodium amide, sodium hydride, tertiary amines (e.g. triethylamine and tripropylamine), pyridine and quinoline. The desirable amount of the compound (11) used is generally at least 1 mole, preferably 1–2 moles per mole of the compound (12). The reaction is desirably conducted generally at room temperature to 150° C., preferably at room temperature to 100° C. and is complete generally in about 1.5–15 hours.

Successively, hydrolysis is conducted by a treatment in the presence of a mineral acid such as hydrochloric acid, sulfuric acid or the like, in a solvent such as water, alcohol (e.g., methanol, ethanol or isopropanol), ether (e.g., diethyl ether or tetrahydrofuran) or the like, at room temperature to the boiling point of the solvent used, for 30 minutes to 15 hours.

The reaction of the compound (13) with malonic acid (14) is conducted in an appropriate solvent in the presence of a basic compound. The solvent may be any solvent used in the reaction of the compound (1) with the compound (12), or a polar solvent such as pyridine or the like. The basic compound can be exemplified by inorganic bases such as potassium carbonate, sodium carbonate, sodium hydroxide, sodium hydrogencarbonate, sodium amide, sodium hydride and the like, and organic bases such as triethylamine, tripropylamine, piperidine, pyridine, quinoline and the like. The proportions of the compound (13) and malonic acid (14) used are desirably such that the amount of the latter is at least 1 mole, generally 2–7 moles per mole of the former. The reaction is conducted generally at 0°–200° C., preferably at about 70°–150° C. and is complete in about 1–10 hours.

The reaction for converting the compound (15) into a compound (1) is conducted, for example, by reducing the compound (15) with a catalyst for catalytic reduction, in an appropriate solvent. The solvent includes, for example, water; acetic acid; alcohols such as methanol, ethanol, isopropanol and the like; hydrocarbons such as hexane, cyclohexane and the like; ethers such as diethylene glycol dimethyl ether, dioxane, tetrahydrofuran, diethyl ether and the like; esters such as ethyl acetate, methyl acetate and the like; and aprotic polar solvents such as N,N-dimethylformamide and the like. As to the catalyst for catalytic reduction, there are used, for example, palladium, palladium black, palladium-carbon, platinum, platinum oxide, copper chromite and Raney nickel. The amount of the catalyst used is desirably 0.02–1 time the weight of the compound (15). The reaction is conducted at a hydrogen pressure of 1–10 atm. generally at about room temperature to 200° C., preferably at about 50°–150° C., and is complete in about 0.5–10 hours. The reaction proceeds favorably by the addition of a basic compound (e.g., triethylamine) to the reaction system.

In the reaction formula-3 and the Reaction Formula-4, when an optically active compound is used as the compound (10) or (12), an optically active compound (1) can be obtained.

In each of the above reaction formulas, the compounds (3), (5), (9), (10) and (12) each used as a starting material can be produced, for example, by the processes represented by the following reaction formulas.

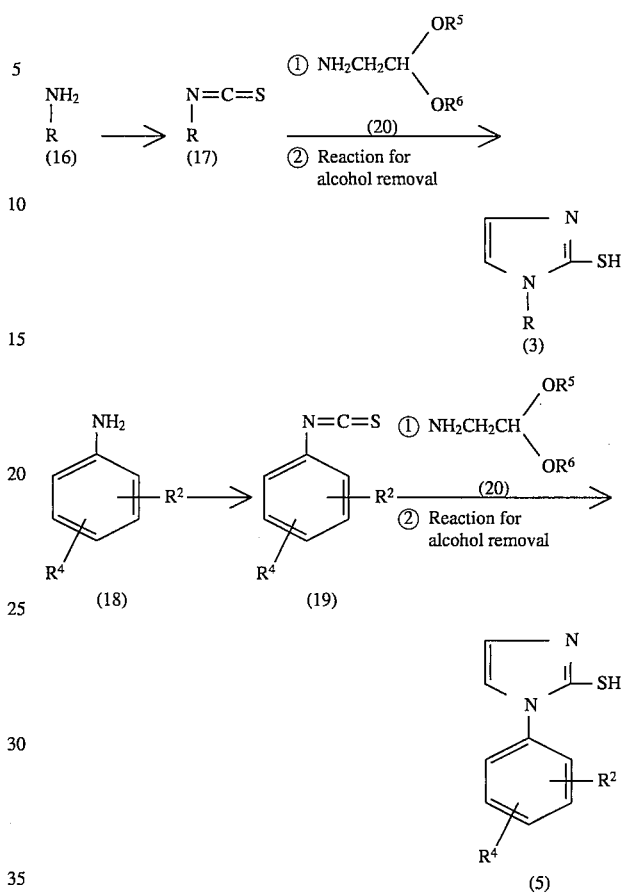

(wherein, R, $R^2$, $R^4$, $R^6$ and $R^7$ are the same as defined above).

The reaction for converting the compound (16) into a compound (17) and the reaction for converting the compound (18) into a compound (19) can be conducted by (1) reacting the compound (16) or (18) with thiophosgene in an appropriate solvent or (2) reacting the compound (16) or (18) with carbon disulfide in an appropriate solvent in the presence of a basic compound, and successively reacting the reaction product with a dehydrating agent such as dicyclohexylcarbodiimide, carbonylimidazole or the like in an appropriate solvent.

The solvent used in the above reaction (1) may be any solvent which does not adversely affect the reaction, and can be exemplified by alcohols such as ethanol, methanol, isopropanol and the like; halogenated hydrocarbons such as chloroform, dichloromethane, carbon tetrachloride and the like; aromatic hydrocarbons such as benzene, toluene, xylene and the like; ethers such as dioxane, diethylene glycol dimethyl ether, diethyl ether, tetrahydrofuran and the like; and polar solvents such as dimethyl sulfoxide, hexamethylphosphoric triamide and the like. The reaction (1) is conducted generally at room temperature to 150° C., preferably at about room temperature to 100° C. and is complete in about 1–10 hours. The desirable amount of the compound (16) or (18) used is at least 1 mole, preferably 1–3 moles per mole of thiophosgene.

The solvent used in the above reaction (2) may be any solvent used in the reaction (1) or other solvent such as pyridine or the like. The basic compound can be exemplified by inorganic bases such as sodium hydroxide, potassium hydroxide, sodium carbonate, sodium hydrogencarbonate, potassium hydrogencarbonate, potassium carbonate, sodium methoxide, sodium ethoxide, sodium hydride, metallic sodium, metallic potassium, sodium amide and the like, and organic bases such as N,N-dimethylaniline, piperidine, pyridine, triethylamine, sodium acetate, potassium acetate and the like. The reaction (2) is conducted generally at 0°–100° C., preferably at 0°–70° C. and is complete generally in about 1–15 hours. The desirable amount of carbon disulfide used is generally 1–20 moles, preferably 1–10 moles per mole of the compound (16) or (18).

In the subsequent reaction with a dehydrating agent, the solvent used may be any solvent used in the above reaction of the compound (16) or (18) with carbon disulfide. The reaction is conducted generally at 0°–100° C., preferably at 0°–70° C. and is complete generally in about 1–15 hours. The desirable amount of the dehydrating agent used is at least 1 mole, preferably 1–2 moles per mole of the compound (16) or (18).

The reaction of the compound (17) with the compound (20) and the reaction of the compound (19) with the compound (20) are conducted in the presence of an appropriate solvent or in the absence of any solvent. The solvent may be any solvent mentioned in the reaction (1) for converting the compound (16) or (18) into a compound (17) or (19). The reaction is conducted generally at 0°–200° C., preferably at about 0°–150° C. and is complete generally in about 5 minutes to 5 hours. The desirable amount of the compound (20) used is at least 1 mole, preferably 1–2 moles per mole of the compound (17) or (19).

The subsequent reaction for alcohol removal is conducted in an appropriate solvent or in the absence of any solvent, in the presence of a mineral acid such as hydrochloric acid, sulfuric acid or the like at room temperature to 150° C., preferably at about room temperature to 120° C., and is complete in about 10 minutes to 10 hours. The solvent used can be exemplified by water; alcohols such as methanol, ethanol, isopropanol and the like; ethers such as diethyl ether, tetrahydrofuran and the like; and mixtures thereof.

Reaction formula-6

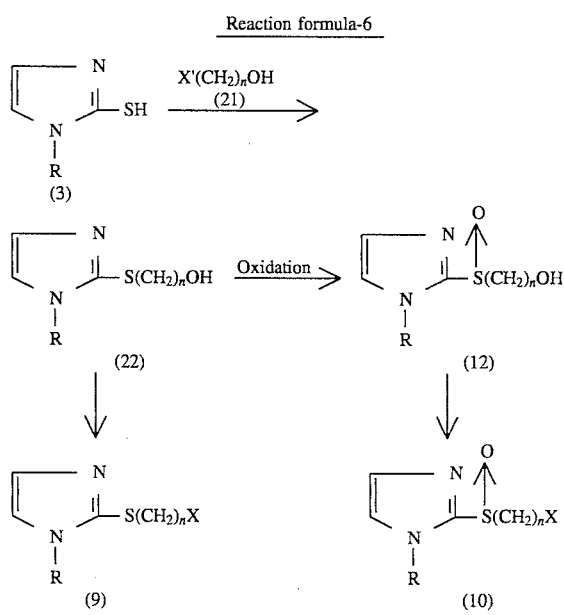

(wherein, R, n, $X^1$ and X are the same as defined above).

The reaction of the compound (3) with the compound (21) is conducted under the same conditions as in the Reaction of the compound (2) with the compound (3) in the Reaction formula-1. The oxidation of the compound (22) is conducted under the same conditions as in the oxidation of the compound (4) in the Reaction formula-1.

The reaction for converting the compound (22) into a compound (9) and the reaction for converting the compound (12) into a compound (10) are conducted as follows. For example, when X is a halogen atom in the compound (9) or (10), said reactions are each conducted in the presence of a halogenating agent in an appropriate solvent or in the absence of any solvent. The halogenating agent can be exemplified by hydrohalogenic acids such as hydrochloric acid, hydrobromic acid and the like; N,N-diethyl-1,2,2-trichlorovinylamide; phosphorus pentabromide; phosphorus oxychloride; and thionyl chloride. The desirable amount of the halogenating agent used is at least equimolar, generally a large excess over the compound (22) or (12). The solvent can be exemplified by ethers such as dioxane, tetrahydrofuran, diethyl ether and the like, and halogenated hydrocarbons such as chloroform, methylene chloride, carbon tetrachloride and the like. The above reactions each proceed generally at −20° C. to 150° C., preferably at −20° C. to 80° C., and are complete generally in about 10 minutes to 6 hours.

When X is a lower alkanesulfonyloxy group, an arylsulfonyloxy group or an aralkylsulfonyloxy group in the compound (9) or (10), each reaction is conducted by reacting the compound (22) or (12) with a compound represented by general formula $R^8X^1$ (23) ($R^8$ is a lower alkanesulfonyl group, an arylsulfonyl group or an aralkylsulfonyl group, and $X^1$ is the same as defined above) in an appropriate solvent in the presence of a basic compound. The solvent and the basic compound can each be any one described in the reaction of the compound (2) with the compound (3) in the Reaction formula-1. Each reaction is conducted generally at 0°–200° C., preferably at about 0°–100° C., and is complete generally in about 5 minutes to 10 hours. The desirable amount of the compound (23) used is at least 1 mole, preferably 1–2 moles per mole of the compound (22) or (12).

Each of the intended compounds obtained by the above reaction formulas can be easily separated from the reaction system and purified by ordinary means. The means for separation can be exemplified by solvent extraction, dilution, recrystallization, column chromatography and preparative thin-layer chromatography.

Needless to say, the compounds of the present invention include optical isomers and stereoisomers.

Each of the compounds of the present invention is used generally in the form of ordinary pharmaceutical preparation. The pharmaceutical preparation is prepared by using diluents or excipients ordinarily used, such as filler, bulking agent, binder, humectant, disintegrator, surfactant, lubricant and the like. The pharmaceutical preparation can be prepared in various forms depending upon the purpose of remedy, and the typical forms include tablets, pills, a powder, a solution, a suspension, an emulsion, granules, capsules, suppositories, an injection (e.g. solution or suspension), etc. In preparing tablets, there can be used various carriers known in the art. The carriers can be exemplified by excipients such as lactose, white sugar, sodium chloride, glucose, urea, starch, calcium carbonate, kaolin, crystalline cellulose, silicic acid and the like; binders such as water, ethanol, propanol, simple syrup, glucose solution, starch solution, gelatin solution, carboxymethyl cellulose, shellac, methyl cellulose, potassium phosphate, polyvinylpyrrolidone and the like; disintegrators such as dry starch, sodium alginate, powdered agar, powdered laminarin, sodium hydrogencarbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promoters such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like. The tablets can be prepared, as necessary, in the form of ordinary coated tablets, such as sugar-coated tablets, gelatin-coated tablets, enteric coated tablets or film-coated tablets, or in the form of double-layered tablets or multi-layered tablets. In preparing pills, there can be used various carriers known in the art. The carriers can be exemplified by excipients such as glucose, lactose, starch, cacao butter, hardened vegetable oils, kaolin, talc and the like; binders such as powdered acacia, powdered tragacanth, gelatin, ethanol and the like; and disintegrators such as laminarin, agar and the like. In preparing suppositories, there can be used carriers known in the art. The carriers can be exemplified by a polyethylene glycol, cacao butter, a higher alcohol, a higher alcohol ester, gelatin and a semi-synthetic glyceride. In preparing an injection (solution, emulsion or suspension), it is sterilized and is preferably made isotonic to the blood. In preparing the solution, emulsion or suspension, there can be used all diluents ordinarily used in the art, such as water, aqueous lactic acid solution, ethyl alcohol, propylene glycol, ethoxylated isostearyl alcohol, polyoxy-isostearyl alcohol and polyoxyethylene sorbitan-fatty acid esters. In this case, the injection may contain sodium chloride, glucose or glycerine in an amount sufficient to make the injection isotonic, and may further contain a solubilizing agent, a buffer solution, a soothing agent, etc. all ordinarily used. The pharmaceutical preparation may furthermore contain, as necessary, a coloring agent, a preservative, a perfume, a flavoring agent, a sweetening agent and other drugs. In preparing the present pharmaceutical preparation in the form of a paste, a cream or a gel, there can be used diluents such as white petrolatum, paraffin, glycerin, cellulose derivatives, polyethylene glycol, silicon, bentonite and the like.

The amount of the compound of general formula (1) or the salt thereof to be contained in the pharmaceutical preparation of the present invention is not particularly restricted and can be appropriately selected from a wide range, but the desirable amount is generally 1–70% by weight in the pharmaceutical preparation.

The method for administering the pharmaceutical preparation of the present invention is not particularly restricted. It is decided depending upon the form of preparation, the age, distinction of sex and other conditions of patient, the disease condition of patient, etc. For example, tablets, pills, a solution, a suspension, an emulsion, granules or capsules are administered orally. An injection is intravenously administered singly or in admixture with an ordinary auxiliary solution of glucose, amino acids or the like, or, as necessary, is singly administered intramuscularly, intradermally, subcutaneously or intraperitoneally. Suppositories are administered intrarectally.

The dose of the pharmaceutical preparation of the present invention is appropriately selected depending upon the administration method, the age, distinction of sex and other conditions of patient, the disease condition of patient, etc., but the desirable dose is generally about 0.06–100 mg per kg of body weight per day in terms of the amount of the active ingredient, i.e. the compound of general formula (1) or the salt thereof. The pharmaceutical preparation can be administered in 2 to 4 portions in a day.

The present invention is hereinafter described specifically by way of Preparation Examples, Reference Examples, Examples and Pharmacological Test.

PREPARATION EXAMPLE 1

Preparation of tablets

| Component | Amount (g) |
| --- | --- |
| 6-{3-[1-(2-Nitrophenyl)-2-imidazolyl]-sulfinylpropoxyl}-3,4-dihydrocarbostyril | 5 |
| Lactose (Japanese Pharmacopoea grade) | 50 |
| Corn starch (Japanese Pharmacopoea grade) | 25 |
| Crystalline cellulose (Japanese Pharmacopoea grade) | 25 |
| Methyl cellulose (Japanese Pharmacopoea grade) | 1.5 |
| Magnesium stearate (Japanese Pharmacopoea grade) | 1 |

The above compound of the present invention, lactose, corn starch and crystalline cellulose were mixed thoroughly. The mixture was made into granules using a 5% aqueous methyl cellulose solution. The granules were passed through a 200-mesh sieve and then dried carefully. The dried granules were made into 1,000 tablets by an ordinary method.

PREPARATION EXAMPLE 2

Preparation of capsules

| Component | Amount (g) |
| --- | --- |
| 6-{3-[1-(2,4-Difluorophenyl)-2-imidazolyl)-sulfinylpropoxy]-3,4-dihydrocarbostyril | 10 |
| Lactose (Japanese Pharmacopoea grade) | 80 |
| Starch (Japanese Pharmacopoea grade) | 30 |
| Talc (Japanese Pharmacopoea grade) | 5 |
| Magnesium stearate (Japanese Pharmacopoea grade) | 1 |

The above components were finely ground and thoroughly mixed to obtain a uniform mixture. The mixture was filled into gelatin capsules for oral administration, each having a desired dimension, whereby 1,000 capsules were prepared.

PREPARATION EXAMPLE 3

Preparation of injection

| Component | Amount (g) |
| --- | --- |
| 6-{3-[1-(2-Trifluoromethylphenyl)-2-imidazolyl]sulfinylpropoxy}-3,4-dihydrocarbostyril | 1 |
| Polyethylene glycol (molecular weight: 4,000) (Japanese Pharmacopoea grade) | 0.3 |
| Sodium chloride (Japanese Pharmacopoea grade) | 0.9 |
| Polyoxyethylene sorbitan monooleate (Japanese Pharmacopoea grade) | 0.4 |
| Sodium metabisulfite | 0.1 |
| Methyl parahydroxybenzoate (Japanese Pharmacopoea grade) | 0.18 |
| Propyl parahydroxybenzoate | 0.02 |

| Component | Amount (g) |
| --- | --- |
| (Japanese Pharmacopoea grade) Distilled water for injection | 100 (ml) |

The above parahydroxybenzoates, sodium metabisulfite and sodium chloride were dissolved in distilled water of about half of the above volume at 80° C., with stirring. The solution was cooled to 40° C., and therein were dissolved the compound of the present invention, polyethylene glycol and polyoxyethylene sorbitan monooleate. To the resulting solution was added the remaining volume of distilled water for final volume adjustment, followed by filtration through an appropriate filter paper for sterilization, whereby an injection was prepared.

Reference Example 1

To 200 ml of benzene were added 22 g of 2-nitroaniline and 6.6 ml of thiophosgene. The mixture was refluxed for 2 hours. After cooling, the resulting crystals were removed by filtration and the filtrate was concentrated. The resulting residue was purified by a silica gel column chromatography (eluant: ethyl acetate/n-hexane=0/1→1/10) to obtain 8.0 g of 2-nitrophenyl isothiocyanate.

$^1$H-NMR (CDCl$_3$) δ ppm:
7.35–7.50 (2H, m), 7.63 (1H, m),
8.09 (1H, d, J=8 Hz)

Reference Example 2

In 800 ml of pyridine were dissolved 275 ml of carbon disulfide and 93 ml of triethylamine. To the solution was added 125 g of 4-bromo-2-methylaniline. The mixture was stirred at room temperature overnight. Thereto was added 138.5 g of 1,3-dicyclohexylcarbodiimide (DCC). The mixture was stirred overnight. Pyridine was removed by distillation. To the residue was added n-hexane. The resulting precipitate (DC-thiourea) was removed by filtration. The filtrate was concentrated and the residue was purified by a silica gel column chromatography (eluant: n-hexane) to obtain 138 g of 4-bromo-2-methylphenyl isothiocyanate.

White acicular crystals.

Melting point: 43°–45° C.

Reference Example 3

147 Grams of 2,4-difluorophenyl isothiocyanate was obtained by using 100 ml of 2,4-difluoroaniline, 138 ml of triethylamine, 400 ml of carbon disulfide, 500 ml of pyridine and 206 g of DCC and by using the same procedure as in Reference Example 2.

Colorless oil.

$^1$H-NMR (CDCl$_3$) δ ppm:
6.8–7.0 (2H, m), 7.17 (1H, m)

Reference Example 4

105.5 Milliliters of 2,2-diethoxyethylamine was dropwise added to 138 g of 4-bromo-2-methylphenyl isothiocyanate with ice-cooling. The mixture was stirred for 10 minutes and then further stirred for 10 minutes at 100° C. The mixture was allowed to cool, and thereto was added 500 ml of 8 N hydrochloric acid. The mixture was refluxed for 2 hours. The resulting crystals were collected by filtration, washed with water thoroughly and then dried to obtain 110 g of 1-(4-bromo- 2-methylphenyl)-2-mercaptoimidazole.

White prismatic crystals.

Melting point: 241° C. (decomposed)

Reference Example 5

118 Grams of 1-(2,4-difluorophenyl)-2-mercaptoimidazole was obtained by using 147 g of 2,4-difluorophenyl isothiocyanate, 150 ml of 2,2-diethoxyethylamine and 150 ml of 6 N hydrochloric acid and by using the same procedure as in Reference Example 4.

White powder.

$^1$H-NMR (CDCl$_3$) δ ppm:
6.91 (1H, s), 6.94 (1H, s), 7.0–7.2 (2H, m), 7.7 (1H, m)

Reference Example 6

2.5 Grams of 1-(2-nitrophenyl)-2-mercaptoimidazole was obtained by using 6 g of 2-nitrophenyl isothiocyanate, 5.8 ml of 2,2-diethoxyethylamine and 100 ml of 6 N hydrochloric acid and by using the same procedure as in Reference Example 4.

$^1$H-NMR (DMSO-d$_6$) δ ppm:
7.12 (1H, s), 7.32 (1H, s), 7.61 (1H, d, J=7 Hz), 7.74 (1H, dd, J=7.8 Hz), 7.90 (1H, dd, J=7.8 Hz), 8.16 (1H, d, J=8 Hz)

Reference Example 7

In 300 ml of dimethylformamide were dissolved 89 g of 6-(3-chloropropoxy)-3,4-dihydrocarbostyril and 110 g of 1-(4-bromo-2-methylphenyl)-2-mercaptoimidazole. To the solution was slowly added 66.7 g of potassium carbonate at room temperature. The mixture was stirred at 80° C. for 2 hours to give rise to a reaction. After the completion of the reaction, the reaction mixture was extracted with ethyl acetate. The oily layer was washed with water thoroughly, washed with an aqueous solution saturated with sodium chloride, dried with anhydrous magnesium sulfate, and subjected to distillation to remove the solvent. The resulting brown oil was purified by a silica gel column chromatography (eluant: chloroform/methanol=50/1). The resulting crude crystals were recrystallized from ethanol to obtain 118 g of 6-{3-[1-(2-methyl-4-bromophenyl)-2-imidazolylthio] propoxy}- 3,4-dihydrocarbostyril.

Colorless prismatic crystals.

Melting point: 117°–120° C.

Reference Example 8

42.4 Grams of 6-{3-(2,4-difluorophenyl)-2-imidazolylthio]propoxy-3,4-dihydrocarbostyril was obtained by using 40 g of 6-(3-chloropropoxy)-3,4-dihydrocarbostyril, 42.6 g of 1-(2,4-difluorophenyl)-2-mercaptoimidazole, 36 ml of DBU and 600 ml of isopropanol and by using the same procedure as in Reference Example 7.

White prismatic crystals (recrystallized from ethanol-n-hexane).

Melting point: 133°–134° C.

Reference Example 9

To 800 ml of dichloroethane sufficiently dried with a molecular sieve were added 52.5 ml of titanium tetraisopropoxide and 119.2 ml of D-(–)-diethyl tartarate. The mixture was stirred for 30 minutes. In the solution was dissolved 82 g of 6-{3-[1-(2-methyl-4-bromophenyl)- 2-imidazolylthio]propoxy}-3,4-dihydrocarbostyril. Thereto was added 0.78 ml of water. The mixture was stirred for 30 minutes. The reactor inside was sufficiently purged with nitrogen, and the reactor contents were cooled with methanol-ice. Thereto was added 103.8 ml of cumene hydroperoxide. The mixture was stirred to 5° C. for 64 hours to give rise to a reaction. After the completion of the reaction, the reaction mixture was purified by a silica gel column chromatography (eluant: dichlorometane/ethyl acetate/methanol=30/10/1), followed by three times of recrystallization from ethanol, to obtain 24.5 g of (S)-(+)-6-{3-[1-(2-methyl- 4-bromophenyl)-2-imidazolylsulfinyl]propoxy}-3,4-dihydrocarbostyril.

Colorless prismatic crystals.

Optical purity: nearly 100% (enantiomer excess)

$[\alpha]_D^{24}$: 19.6° (c=1.0, methanol)

Melting point: 156°–158° C.

The high performance liquid chromatography used for measurement of optical purity was conducted under the following conditions.

Column: DAICEL CHIRALCEL OJ 4.6 mm×250 mm (a product of DAICEL CHEMICAL INDUSTRIES, LTD.)

Mobile phase: n-hexane/isopropanol/diethylamine=400/600/1

Flow rate: 0.6 ml/min

Ultraviolet light: 254 nm

Retention time: 34.5 minutes

Reference Example 10

380 Grams of 1-(2-methylphenyl)-2-mercaptoimidazole, 300 g of potassium carbonate and 400 g of 3-chlolopropanol were mixed with 5 l of dimethylformamide. The mixture was stirred at 60° C. for 5 hours. The reaction mixture was filtered and the filtrate was subjected to distillation under reduced pressure. The residue was dissolved in ethyl acetate. The solution was washed with an aqueous solution saturated with sodium chloride, dried with anhydrous magnesium sulfate, and subjected to distillation to remove the solvent. The residue was dissolved in 1 l of a 1:2 mixture of diethyl ether and n-hexane. The solution was allowed to stand in an ice bath to obtain 430 g of 3-[1-(2-methylphenyl)- 2-imidazolylthio]propanol.

Colorless acicular crystals.

Melting point: 47°–48° C. (recrystallized from diethyl ether-n-pentane)

$^1$H-NMR (CDCl$_3$) δ ppm: 1.7–1.95 (2H, m), 2.09 (3H, s), 3.32 (2H, t, J=7 Hz), 3.74 (2H, t, J=7 Hz), 5.83 (1H, brs), 6.96 (1H, d, J=2 Hz), 7.12 (1H, d, J=2 Hz), 7.21 (1H, d, J=7 Hz), 7.27–7.45 (3H, m)

Reference Example 11

To 3 l of dichloroethane were added 123 g of 3-[1-(2-methylphenyl)-2-imidazolylthio]propanol, 414 g of L-(+)-diethyl tartarate and 120 g of a powder of Molecular Sieve 4A. The mixture was stirred at room temperature for 2 days. Thereto was added 142 g of titanium tetraisopropoxide. The mixture was stirred at room temperature for 30 minutes. Thereto was added 91 g of cumene hydroperoxide. The mixture was stirred at 5° C. for 24 hours. The reaction mixture per se was purified by a silica gel column chromatography (eluant: dichloromethane/methanol=50/1). Recrystallization from methyl ethyl ketone was repeated to obtain 50 g of (S)-(+)-3-[1-(2-methylphenyl)2-imidazolylsulfinyl]propanol.

Colorless acicular crystals.

Optical purity: 100% (enantiomer excess)

$[\alpha]_D^{24}$: 67.5° (C=1.0, methanol)

Melting point: 111°–111.5° C.

$^1$H-NMR (CDCl$_3$) δ ppm: 1.95–2.25 (5H, m), 2.88 (1H, m), 3.40–3.80 (4H, m), 7.15 (1H, d, J=2 Hz), 7.28–7.55 (5H, m)

The high performance liquid chromatography used for measurement of optical purity was conducted under the following conditions.

Column: DAICEL CHIRALCEL OJ 4.6 mm×250 mm (a product of DAICEL CHEMICAL INDUSTRIES, LTD.)

Mobile phase: n-hexane/ethanol/diethylamine=800/200/1

Flow rate: 1.0 ml/min

Ultraviolet light: 254 nm

Retention time: 18.5 minutes

Reference Example 12

To 50 ml of dimethylformamide were added 2.9 g of 3-[1-(2-methylphenyl)-2-imidazolylsulfinyl]propanol and 3.4 g of 5-chloro-2-nitro-benzaldehyde dimethylacetal. To the mixture being stirred was added 0.75 g of 60% sodium hydride slowly. The mixture was stirred at 60° C. overnight. Thereto was added an aqueous solution saturated with ammonium chloride. The reaction mixture was concentrated. The residue was extracted with ethyl acetate. The extract was washed with water and an aqueous solution saturated with sodium chloride, dried with magnesium sulfate, and subjected to distillation to remove ethyl acetate. The residue was purified by a silica gel column chromatography (eluant: dichloromethane/methanol=1/0→50/1) to obtain 3.3 g of 1-(2-methylphenyl)-2-[3-(3-dimethoxymethyl-4-nitrophenoxy)propylsulfinyl]imidazole as a light yellow oil.

$^1$H-NMR (CDCl$_3$) δ ppm: 2.11 (3H, brs), 2.2–2.4 (2H, m), 3.43 (6H, s), 3.50 (1H, m), 3.70 (1H, m), 4.1–4.3 (2H, m), 6.00 (1H, s), 6.85 (1H, dd, J=3 Hz, 9 Hz), 7.18 (1H, s), 7.2–7.5 (5H, m), 7.25 (1H, d, J=3 Hz), 7.95 (1H, d, J=9 Hz)

Reference Example 13

3.3 Grams of 1-(2-methylphenyl)-2-[3-(3-dimethoxymethyl- 4-nitrophenoxy)propylsulfinyl]imidazole was added to 100 ml of tetrahydrofuran and 10 ml of 4 N hydrochloric acid. The mixture was stirred overnight and extracted with ethyl acetate. The extract was washed with water and an aqueous solution saturated with sodium chloride, dried with magnesium sulfate, and concentrated to obtain 2.8 g of 1-(2-methylphenyl)-2-[3-( 3-formyl-4-nitrophenoxy)propylsulfinyl]imidazole as a light yellow oil.

$^1$H-NMR (CDCl$_3$) δ ppm: 2.11 (3H, brs), 2.2–2.45 (2H, m), 3.47 (1H, m), 3.75 (1H, m), 4.2–4.35 (2H, m), 7.10 (1H, dd, J=3 Hz, 9 Hz), 7.15–7.5 (7H, m), 8.15 (1H, d, J=9 Hz), 10.47 (1H, s)

Reference Example 14

To 100 ml of pyridine were added 5.0 g of 1-( 2-methylphenyl)-2-[3-(3-formyl-4-nitrophenoxy)propylsulfinyl]imidazole, 2.0 g of malonic acid and 2 ml of piperidine. The mixture was refluxed for 2.5 hours. The reaction mixture was subjected to distillation to remove pyridine. The residue was made alkaline with an aqueous potassium carbonate solution. The resulting solution was washed with ethyl acetate and extracted with dichloromethane. The methylene chloride layer was dried with magnesium sulfate and then concentrated. The residue was recrystallized from ethanol to obtain 1.7 g of 2-nitro-5-{3-[1-(2-methylphenyl)-2-imidazolyl)sulfinyl]propoxy}cinnamic acid.

$^1$H-NMR (CDCl$_3$) δ ppm: 1.9–2.2 (5H, m), 3.4 (1H, m), 3.55 (1H, m), 4.2–4.6 (2H, m), 6.53 (1H, s, J=16 Hz), 7.14 (1H, d, J=9 Hz), 7.29 (1H, s), 7.3–7.55 (5H, m), 7.67 (1H, s), 7.96 (1H, d, J=16 Hz), 8.11 (1H, d, J=9 Hz), 12.71 (1H, brs)

Example 1

In a pressure glass reactor containing ethanol was placed 12 g of 6-{3-[1-(2-methyl-4-bromophenyl)-2-imidazolylsulfinyl]propoxy}-3,4-dihydrocarbostyril. To the resulting solution were added 18 ml of triethylamine and 6 g of a 10% palladium carbon powder. The reactor inside was purged with hydrogen gas and the reactor contents were subjected to a reaction at a pressure of 3 kg/cm$^2$ at 70° C. for 16 hours. The reaction was repeated on the same scale. The reaction mixture obtained from two times of the reaction was filtered to remove the catalyst. The filtrate was extracted with chloroform, washed with 1 N aqueous hydrochloric acid solution thoroughly, washed with an aqueous solution saturated with sodium chloride, dried with anhydrous magnesium sulfate, and subjected to distillation to remove the solvent. The resulting white oil was purified by a silica gel column chromatography (eluant: dichloromethane/ethyl acetate/methanol=30/10/1) to obtain crude crystals. The crude crystals were recrystallized from ethanol to obtain 13.2 g of (S)-(+)-6-{3-[1-(2-methylphenyl)- 2-imidazolylsulfinyl]propoxy}-3,4-dihydrocarbostyril.

White powdery crystals.

Optical purity: 99.4% (enantiomer excess)

$[α]_D^{24}$: 17.2° (c=1.0, methanol)

Melting point: 124.5°–126.5° C.

The high performance liquid chromatography used for measurement of optical purity was conducted under the following conditions.

Column: ULTRON ES-OVM 4.6 mm×150 mm (a product of Shinwa Chemical Industries, Ltd.)

Mobile phase: acetonitrile/20 mM KH$_2$PO$_4$ aq.=8/92

Flow rate: 0.8 ml/min

Ultraviolet light: 254 nm

Retention time: 16.5 minutes

The same conditions were used also in Example 2 and Example 5 which follow.

Example 2

3.97 Grams of (S)-(+)-3-[1-(2-methylphenyl)-2-imidazolylsulfinyl]propanol and 2.72 ml of triethylamine were mixed with 80 ml of ethyl acetate. Thereto was added 1.51 ml of methanesulfonyl chloride at room temperature, and the mixture was stirred for 10 minutes. The reaction mixture was washed with an aqueous sodium hydrogencarbonate solution and a saturated aqueous sodium chloride solution in this order, dried with magnesium sulfate, and subjected to distillation to remove the solvent. The residue was dissolved in 20 ml of dimethyl sulfoxide. This solution is referred to as "solution A".

8.35 Grams of sodium salt of 6-hydroxy-3,4-dihydrocarbostyril was mixed with 80 ml of dimethyl sulfoxide. Thereto was added solution A at 60° C., and the mixture was stirred for 0.5 hour under the same state. The reaction mixture was dissolved in ethyl acetate. The solution was washed with an aqueous solution saturated with sodium chloride, dried with anhydrous magnesium sulfate, and subjected to distillation to remove the solvent. The residue was purified by a silica gel column chromatography (eluant: dichloromethane/methanol=40/1). The crude crystals were recrystallized from ethanol to obtain 4.5 g of (S)-(+)-6-{3-[1-(2-methylphenyl)-2-imidazolylsulfinyl]propoxy}-3,4-dihydrocarbostyril.

White powder.

Optical purity: 99.7% (enantiomer excess)

$[α]_D^{24}$: 17.2° (c=1.0, methanol)

Melting point: 124.5°–126.5° C.

Example 3

To 50 ml of ethanol were added 300 mg of 2-nitro-5-{3-[1-(2-methylphenyl)-2-imidazolylsulfinyl]propoxy}cinnamic acid, 100 mg of 10% palladium carbon and 0.6 ml of triethylamine. Hydrogenation was conducted at a hydrogen pressure of 4 atm. at 60° C. for 3 hours. The reaction mixture was cooled to room temperature and filtered to remove the catalyst. To the filtrate was added 200 mg of 10% palladium carbon, and hydrogenation was conducted at a hydrogen pressure of 4 atm. at 60° C. for 6 hours. Ethanol was removed by distillation. The residue was made acidic with hydrochloric acid, followed by extraction with methylene chloride. The extract was washed with an aqueous solution saturated with sodium chloride, dried with anhydrous magnesium sulfate, and subjected to distillation to remove the solvent. The residue was purified by a silica gel column chromatography (eluant: dichloromethane/methanol=50/1→20/1). The crude crystals were recrystallized from ethanol-n-hexane to obtain 70 mg of 6-{3-[1-(2-methylphenyl)-2-imidazolylsulfinyl]propoxy}-3,4-dihydrocarbostyril.

White powder.

Melting point: 141.5°–142.5° C.

Example 4

In 1 liter of dichloromethane was dissolved 67 g of 6-{3-[1-(2-methylphenyl)-2-imidazolylthio]propoxy}- 3,4-dihydrocarbostyril. Thereto was added 32.6 g of m-chloroperbenzoic acid with ice-cooling. The mixture was stirred overnight. After the completion of the reaction, the reaction mixture was washed five times with an aqueous solution saturated with sodium hydrogencarbonate, dried with magnesium sulfate, and subjected to distillation to remove the solvent. The residue was purified by a silica gel column chromatography (eluant: dichloromethane/ethyl acetate/methanol=30/10/1). The crude crystals were recrystallized from ethanol-n-hexane to obtain 39.5 g of 6-{3-[1-(2-methylphenyl)-2-imidazolylsulfinyl]propoxy}- 3,4-dihydrocarbostyril.

White powder.

Melting point: 141.5°–142.5° C.

Example 5

To 1 l of 1,2-dichloroethane were added 56.8 g of titanium tetraisopropoxide, 168 g of D-(−)-diethyl tartarate, 0.91 ml of water and 80 g of 6-{3-[1-(2-methylphenyl)- 2-imidazolylthio]propoxy}-3,4-dihydrocarbostyril. The mixture was stirred and then cooled to −5° C. Thereto was added 124 g of cumene hydroperoxide slowly. After the completion of the addition, the mixture was stirred at 5° C. for 18 hours. The reaction was repeated. The reaction mixtures from the two reactions were combined and purified by a silica gel column chromatography (eluant: dichloromethane/ethyl acetate/methanol=3/1/0→30/10/1), followed by recrystallization from ethanol-ethyl acetate. The mother liquor was concentrated to obtain crystals. This procedure was conducted 14 times. The resulting crystals were purified by a silica gel column chromatography (eluant: dichloromethane/ethyl acetate/methanol=30/10/1), followed by recrystallization from ethanol to obtain 2.7 g of (S)-(+)-6-{3-[1-(2-methylphenyl)-2-imidazolylsulfinyl]propoxy}-3,4-dihydrocarbostyril. White powder.

Optical purity: 97.9% (enantiomer excess)

$[\alpha]_D^{24}$: +17.2° (C=1.0, methanol)

Melting point: 124.5°–126.5° C.

Example 6

7.5 g of (R)-(−)-6-{3-[1-(2-methylphenyl)-2-imidazolylsulfinyl]propoxy}-3,4-dihydrocarbostyril was obtained by using 600 ml of dichloroethane, 38.2 ml of titanium tetraisopropoxide, 86.5 ml of L-(+)-diethyl tartarate, 50 g of 6-{3-[1-(2-methylphenyl)-2-imidazolylthio]propoxy}-3,4-dihydrocarbostyril, 75 ml of cumene hydroperoxide and 0.57 ml of water and by using the same procedure as in Example 5. White powder (recrystallized from ethyl acetate).

Optical purity: 96.6% (enantiomer excess)

$[\alpha]_D^{24}$: −16.6° (c=1.0, methanol)

Melting point: 124°–126° C.

The high performance liquid chromatography used for measurement of optical purity was conducted under the following conditions.

Column: ULTRON ES-OVM 4.6 mm×150 mm (a product of Shinwa Chemical Industries, Ltd.)

Mobile phase: acetonitrile/20 mM $KH_2PO_4$ aq.=8/92

Flow rate: 0.8 ml/min

Ultraviolet light: 254 nm

Retention time: 24.5 minutes

The compounds shown in Table 1 were obtained by using suitable starting materials and by using the same procedure as in Examples 1–4.

TABLE 1

| Example No. | R¹ | n | R | Crystal form (Recrystallization solvent) | Melting point (°C.) |
|---|---|---|---|---|---|
| 7 | H | 3 | 2-methylphenyl (CH₃) | White powder (Ethanol-n-hexane) | 141.5–142.5 |
| 8 | H | 3 | 2-nitrophenyl (NO₂) | Yellow powder (Ethanol-diisopropyl ether) | 135 (decomposed) |
| 9 | H | 3 | 2,4-difluorophenyl (F, F) | White powder (Ethanol-n-hexane) | 132–134 |
| 10 | H | 3 | 2-methylphenyl (CH₃) (*) | White powder (Ethanol) | 124.5–126.5 |

TABLE 1-continued

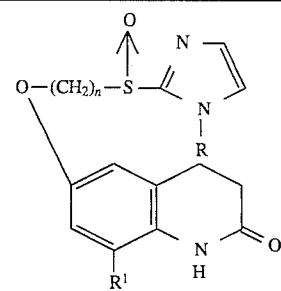

| Example No. | R¹ | n | R | Crystal form (Recrystallization solvent) | Melting point (°C.) |
|---|---|---|---|---|---|
| 11 | H | 3 | (**) 2-CH₃-phenyl | White powder (Ethyl acetate) | 124–126 |
| 12 | H | 3 | 2,3-diF-phenyl (with 3rd F) — 2,3,4-triF-phenyl | Colorless prisms (Ethanol-n-hexane) | 160–161 |
| 13 | H | 3 | 2,4,6-triF-phenyl | White powder (Ethanol-diisopropyl ether) | 157–160 |
| 14 | H | 3 | 2-CF₃-phenyl | White powder (Ethanol-diisopropyl ether) | 141–143 |
| 15 | H | 3 | 2,4,5-triF-phenyl | Colorless prisms (Ethanol-n-hexane) | 133.5–135 |
| 16 | 8-CH₃ | 3 | 2-CH₃-phenyl | White powder (Ethanol-diisopropyl ether) | 137–139.5 |
| 17 | 8-F | 3 | 2,4-diF-phenyl | White powder (Dichloromethane-diethyl ether) | 150–151 |
| 18 | H | 2 | 2,4-diF-phenyl | White powder (Ethanol-diisopropyl ether) | 140–143 |

(*)Compound of Example 10 is a (S)-(+)-form
(**)Compound of Example 11 is a (R)-(−)-form In Table 1, the compound of Example 10 is a (S)-(+) substance and its $[\alpha]_D^{24}$ is 17.2° (c=1 0, methanol). The compound of Example 11 is a (R)-(−) substance and its $[\alpha]_D^{24}$ is −16.6° (c=1.0, methanol).

Pharmacological Test

[Test method]

Wistar strain male rats [6-week age, about 200 g (body weight)] were anesthetized with pentobarbital. Into the thoracic aortic lumen of each anesthetized rat was inserted a balloon catheter (Fogarty 2F manufactured by Baxter Health Care Corporation), and the catheter was expanded to injure, by abrasion, the tunica intima of the thoracic aorta. Then, each rat was allowed to stand at room temperature for 10 minutes under anesthetization. Thereafter, a 10% formalin neutral buffer solution was circulated from the heart of each rat to the whole body under a pressure of about 100 mm $H_2O$ for about 1–2 minutes. The thoracic aorta was separated carefully, refixed and then cut in the crosswise direction to prepare dyed thin slices. Each slice was observed by a microscope to measure the density of platelets adhered onto the injured inside of the thoracic aorta. Each test compound was made into a 5% suspension in acacia; the suspension was orally administered at a dose of 30 mg (test compound)/kg (body weight); and the above test was conducted 1–2 hours after the administration.

[Evaluation]

The density of platelets adhered onto the entire circumference of lumen of each dyed thin slice of thoracic aorta was measured visually by a plurality of examiners. The evaluation of measurement was conducted by the following standard.

−: Platelets are adhered continuously and seen nearly on the entire circumference.

+: Platelets are adhered continuously and seen at some intervals on the circumference.

++: Platelets are adhered continuously in some portions of the circumference and discontinuous in other portions.

+++: Platelets are seen on the entire circumference but only slightly.

TABLE 2

| Test compound | Dosage (mg/kg) | Inhibition of platelets adhesion |
|---|---|---|
| Compound of Example 7 | 30 | +++ |
| Compound of Example 8 | 30 | +++ |
| Compound of Example 9 | 30 | +++ |
| Compound of Example 10 | 30 | ++ |
| Compound of Example 11 | 30 | ++ |
| Compound of Example 12 | 30 | ++ |
| Compound of Example 13 | 30 | ++ |
| Compound of Example 14 | 30 | ++ |
| Compound of Example 15 | 30 | ++ |
| Compound of Example 16 | 30 | ++ |
| Compound of Example 17 | 30 | ++ |
| Compound of Example 18 | 30 | ++ |
| Reference compound A*** | 30 | − |
| | 100 | + |

***Reference compound A is 6-{3-[1-(2-methylphenyl)-2-imidazolyl]-thio-propoxyl-3,4-dihydrocarbostyril (the compound of Example 35 in EP-A-0240015).

In the above test, each test compound was administered to a group of five rats, and there were prepared three slices per each rat.

We claim:

1. A carbostyril compound of the formula (1):

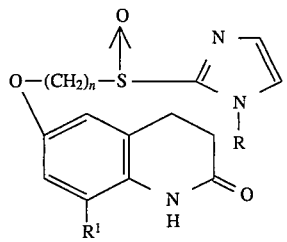

wherein $R^1$ is a hydrogen atom, a fluorine atom or a methyl group; R is a group of the formula:

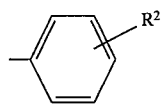

(wherein $R^2$ is a methyl group, a trifluoromethyl group or a nitro group), or a group of the formula

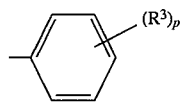

(wherein $R^3$ is a fluorine atom and p is an integer of 2 or 3); and n is an integer of 2 or 3 or a salt thereof.

2. The carbostyril compound of claim 1, wherein $R^1$ is a hydrogen atom.

3. The carbostyril compound of claim 1, wherein $R^1$ is a fluorine atom or a methyl group.

4. The carbostyril compound of claim 2, wherein R is a group of the formula:

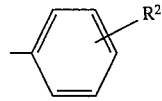

5. The carbostyril compound of claim 2, wherein R is a group of the formula:

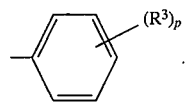

6. The carbostyril compound of claim 3, wherein R is a group of the formula:

7. The carbostyril compound of claim 3, wherein R is a group of the formula

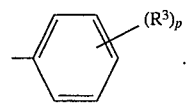

8. The carbostyril compound of claim 4 or 6, wherein $R^2$ is a methyl group.

9. The carbostyril compound of claim 4 or 6, wherein $R^2$ is a trifluoromethyl group or a nitro group.

10. A pharmaceutical composition for inhibiting the adhesion of platelets, which contains as the active ingredient a carbostyril compound or salt thereof of claim 1 and a pharmaceutically acceptable carrier.

11. (S)-(+)-6-{3-[1-(2-Methylphenyl)-2-imidazolylsulfinyl]propoxy}-3,4-dihydrocarbostyril.

12. (R)-(−)-6-{3-[1-(2-Methylphenyl)-2-imidazolylsulfinyl]propoxy}-3,4-dihydrocarbostyril.

13. 6-{3-[1-(2-Methylphenyl)-2-imidazolylsulfinyl]propoxy}-3,4-dihydrocarbostyril.

* * * * *